(12) United States Patent
Fleharty et al.

(10) Patent No.: US 9,988,677 B1
(45) Date of Patent: Jun. 5, 2018

(54) DNA/RNA SEQUENCING USING A SEMICONDUCTING NANOPORE

(71) Applicants: Mark Fleharty, Albuquerque, NM (US); Dimiter N. Petsev, Albuquerque, NM (US); Frank B. Van Swol, Tijeras, NM (US)

(72) Inventors: Mark Fleharty, Albuquerque, NM (US); Dimiter N. Petsev, Albuquerque, NM (US); Frank B. Van Swol, Tijeras, NM (US)

(*) Notice: Subject to any disclaimer, the term of this patent is extended or adjusted under 35 U.S.C. 154(b) by 0 days. days.

(21) Appl. No.: 14/735,898

(22) Filed: Jun. 10, 2015

Related U.S. Application Data

(60) Provisional application No. 62/010,373, filed on Jun. 10, 2014.

(51) Int. Cl.
| | |
|---|---|
| *G01N 27/00* | (2006.01) |
| *G01N 25/18* | (2006.01) |
| *C12Q 1/68* | (2018.01) |
| *G01N 27/327* | (2006.01) |
| *G01N 33/487* | (2006.01) |
| *G01Q 60/24* | (2010.01) |

(52) U.S. Cl.
CPC ....... *C12Q 1/6869* (2013.01); *G01N 27/3278* (2013.01); *G01N 33/48721* (2013.01); *G01Q 60/24* (2013.01)

(58) Field of Classification Search
CPC ............................... G01N 27/00; G01N 25/18
USPC ............... 422/82.02, 68.1; 436/43, 149, 94; 205/775; 435/6.11; 977/700, 704, 904, 977/953, 958
See application file for complete search history.

(56) References Cited

U.S. PATENT DOCUMENTS

| | | | |
|---|---|---|---|
| 9,017,937 B1* | 4/2015 | Turner ................. | C12Q 1/6869 435/6.1 |
| 9,377,433 B2* | 6/2016 | Kulmala ................ | G01N 21/66 |
| 9,677,126 B2* | 6/2017 | Sharaf .................. | C12Q 1/6825 |
| 2003/0040173 A1* | 2/2003 | Fonash et al. ............... | 438/622 |
| 2005/0282229 A1* | 12/2005 | Su et al. ........................ | 435/7.1 |
| 2010/0291548 A1* | 11/2010 | Sharaf .................. | C12Q 1/6816 435/6.11 |

* cited by examiner

*Primary Examiner* — Brian J. Sines
(74) *Attorney, Agent, or Firm* — Gonzales Patent Services; Ellen M. Gonzales

(57) ABSTRACT

The present disclosure provides novel apparatus including, though not necessarily limited to, biosensors utilizing semiconductor materials in electrolyte solutions and methods for using the same. The biosensors rely on a unique property wherein a charged body in the electrolyte solution produces a detectable change in the local conductivity of the semiconductor as the body approaches or travels near the semiconductor.

13 Claims, 2 Drawing Sheets

DNA/RNA SEQUENCING USING A SEMICONDUCTING NANOPORE

CROSS-REFERENCE TO RELATED APPLICATIONS

The following application claims benefit of U.S. Provisional Application No. 62/010,373, filed Jun. 10, 2014, which is hereby incorporated by reference in its entirety.

STATEMENT REGARDING GOVERNMENT SPONSORED RESEARCH

This invention was made with Government support under Grant No. DE-AC04-94AL85000 awarded by the Department of Energy and Sandia National Labs and CBET0844645 awarded by the National Science Foundation. The U.S. Government has certain rights in this invention.

BACKGROUND

Semiconductor materials are materials having an electrical conductivity value falling between conductors like copper and insulators like glass. Examples of semiconductor materials include but are not limited to silicon and germanium. Doped semiconductor materials include impurities which increase the number or change carriers within the semiconductor material.

Electrolyte solutions are solutions containing a ionizing substance dissolved in a solvent. For example, electrolyte solutions can be formed by dissolving a salt in a solvent (such as, but not limited to, water) such that the individual components of the salt dissociate due to the thermodynamic between the solvent and the solute molecules.

The combination of semiconductor materials in electrolyte solutions results in interesting chemical interactions which can be exploited to produce novel technologies in a variety of fields including biosensing and nucleic acid sequencing.

SUMMARY

According to an embodiment, the present disclosure provides novel apparatus including, though not necessarily limited to, biosensors utilizing semiconductor materials in electrolyte solutions. The biosensors rely on a unique property wherein a charged body in the electrolyte solution produces a detectable change in the local conductivity of the semiconductor as the body approaches or travels near the semiconductor. According to yet another embodiment, the present disclosure provides a method for sensing and/or determining the composition of a target body as it passes through the sensor. According to a specific embodiment, determining the composition of the target body comprises sequencing an nucleotide or amino acid sequence.

DETAILED DESCRIPTION

According to an embodiment the present disclosure provides novel apparatus including, though not necessarily limited to, biosensors utilizing semiconductor materials in electrolyte solutions. The biosensors rely on a unique property wherein a charged body in the electrolyte solution produces a detectable change in the local conductivity of the semiconductor as the body approaches or travels near the semiconductor. According to some embodiments the body may be a biopolymer or a portion of a biopolymer. For the purposes of the present disclosure, the term "biopolymer" is intended to include any natural or synthetic nucleic acid, protein, peptide, and naturally or non-naturally occurring variants thereof etc. Accordingly, a portion of a biopolymer could be a single nucleotide, a single amino acid, etc.

According to a specific embodiment, the present disclosure provides a biosensor that can detect individual nucleotides within a nucleic acid strand and produce an ordered and distinguishable signal for each of the identified nucleic acids, thereby sequencing the nucleic acid strand. For the purposes of the present disclosure, a "nucleic acid" or "nucleic acid strand" includes at least one nucleotide, but may include as many as 50, 100, 250, 500 or more nucleotides.

Figure 1:
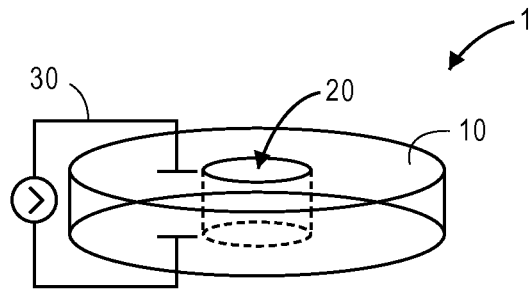
FIG. 1 is a schematic illustration of a sensor according to an embodiment of the present disclosure.

An exemplary sensor according to a first embodiment is shown in FIG. 1. In this embodiment, a detecting unit 1 comprises ring-shaped, doped semiconductor 10 having a pore 20 containing an electrolytic solution. According to some embodiments, the doped semiconductor may be ring-shaped, with a round pore being centrally positioned within the ring, although other shapes for both the semiconductor material and shapes and/or positions for the pore may be utilized. According to various embodiments, the pore may have a diameter that is slightly larger than the body passing through the pore. Accordingly, if the sensor is intended to detect the presence of, or the sequence of, nucleotides, the diameter should be larger enough to allow single nucleotides or a lengthwise strand of nucleotides to pass through the pore, but not so large that the presence of the nucleotides is not detected by the semiconductor. As explained in greater detail below, because the sensor relies on the change of conductivity in the semiconductor that is caused by the presence of a charged body, it may be desirable for the diameter of the pore to be optimized to best reflect this change based on the particular target body that is intended to be detected. A conductivity monitor 30 is in contact with the semiconductor and detects changes in conductivity of the semiconductor that occur as charged bodies in the electrolytic solution flow through the pore. It is important to note that in this embodiment, it is the conductivity variations of the doped semiconductor surrounding the pore that are measured. According to one specific, non-limiting, embodiment, at its most basic, the sensor could consist of a single doped semiconductor material surrounding a pore, an electrolytic solution, and one or more appropriate signal detection mechanisms. Of course those of skill in the art will understand that the sensor could further include a housing including one or more inlets and outlets, one or more fluid control mechanisms and one or more display mechanisms.

Examples of suitable doped semiconductor materials include, but are not limited to n- or p-doped silica. Specific examples include silica doped with phosphorus or other similar species. Examples of suitable electrolyte solutions include salts such as sodium chloride (NaCl), acids such as hydrochloric acid (HCl), bases such as sodium hydroxide (NaOH) or other types of buffers. According to some embodiments, the conductivity monitor may be in communication with a signal generator which may, for example, display a signal correlating to the conductivity of the semiconductor. This may take the form, for example, of the generation of a visual, audible, or otherwise interpretable analog or digital display. In some embodiments, the signal generator may be, include, or communicate with, a computer or processor, which can further interpret the data for the user.

Figure 2A:
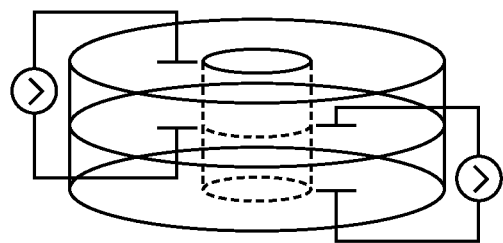
FIG. 2A is a schematic illustration of an embodiment of a stacked sensor according to the present disclosure.
Figure 2B:
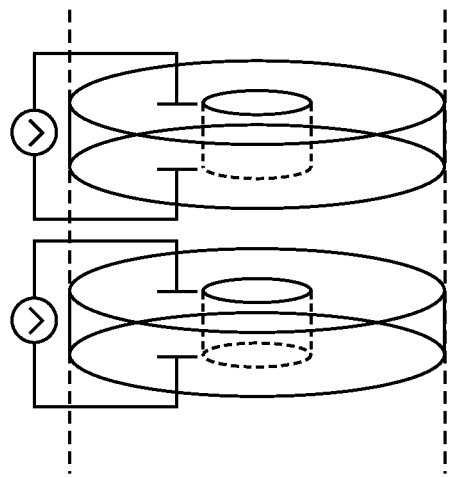
FIG. 2B is a schematic illustration of another embodiment of a stacked sensor according to the present disclosure.

An alternate sensor is shown in FIGS. 2A and 2B. In this embodiment, a stack of detecting units includes a plurality of ring-shaped doped semiconductors. In the depicted embodiment, the various pores within the ring-shaped doped semiconductors are fluidly connected to each other such that a body that travels through one pore will also flow through the other pores. In some embodiments, such as that shown in FIG. 2A, the entire sensor may be viewed as a series of stacked semiconductors surrounding a single pore. The stacked configuration provides a series of detectable signals as the target travels through the pore(s). According to some embodiments, the semiconductors may be identical—that is identically shaped and formed from the same material. Alternatively, the semiconductors could differ in one or more properties. For example, the semiconductors could be formed of the same material, but differently shaped, or similarly or identically shaped but formed from different materials. As a non-limiting example, the stacked semiconductors could include semiconductors formed from n-doped materials and semiconductors formed from p-domed materials, which might provide different, yet complimentary, information. According to some embodiments the sensor may include a plurality of stacked semiconductors, some of which are identical and some of which differ in one or more ways. According to various embodiments, the sensor may include 2, 4, 5, 8, 10, 15, 20 or more semiconductors in a single stack. According to some embodiments the individual detecting units may be stacked such that they are physically touching, as shown in FIG. 2A, or spaced apart as shown in FIG. 2B.

According to another embodiment, the sensor is in communication with or is incorporated into an atomic force microscope such that as samples exit the pore(s), they are subjected to atomic force microscopy.

Figure 3:
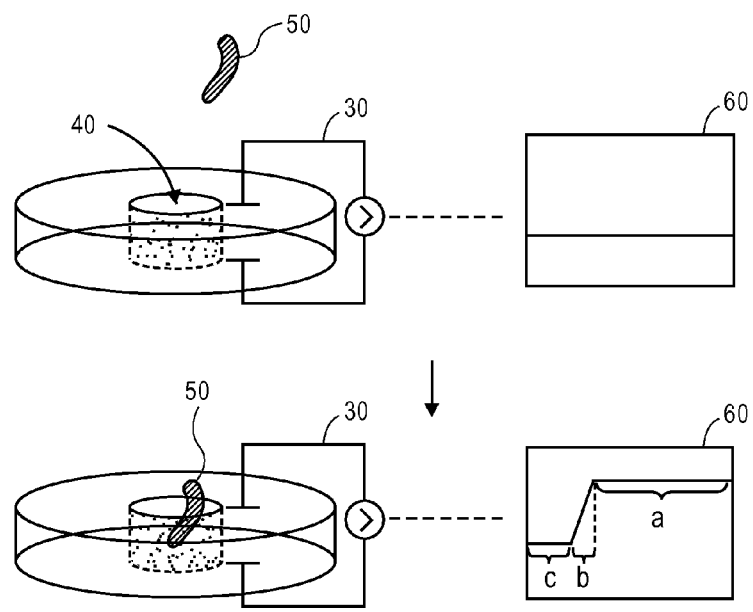
FIG. 3 is a schematic illustration of the sensor of FIG. 1 in use.

FIG. 3 is a schematic illustration of a sensor of the present disclosure detecting the presence of a target body in the electrolyte solution. As shown, the electrolyte solution 40 flows through the pore in the semiconductor and as the charged body 50 approaches the semiconductor, a change in the semi-conductor's conductivity is detected by the conductivity monitor, which is in communication (as illustrated by the dashed lines) with display 60. According to various embodiments, fluid flow can be achieved and/or controlled by pressure difference, electro-osmosis, other gradients such as thermophoresis, or through simply Brownian motion.

In viewing the display graph 60, position "a" indicates the conductivity when the target body 50 is not within range of the pore 40, position "b" indicates the change in conductivity as the target body approaches the pore, ad "c" indicates the changed conductivity as the body travels through the pore. Those of skill in the art will appreciate that the sensor (or apparatus in which the sensor is utilized, integrated, or with which it communicates) could be designed to respond to the detection (or lack of detection) of the change of conductivity in any number of ways including, but not limited to, displaying the change in conductivity (or lack thereof) to a user so as to alert the user to the presence (or absence) of the charged body in the electrolyte solution, and/or automatically starting or ending some other process based on the presence or absence of the target body in the electrolyte solution. In some cases the sensor (or associated apparatus) could be configured to detect the presence (or absence) of a specific charged body within the electrolyte solution based on an anticipated specific change in conductivity while in other cases the sensor could be configured to simply detect the presence (or absence) of any changed body within the electrolyte solution.

Figure 4:
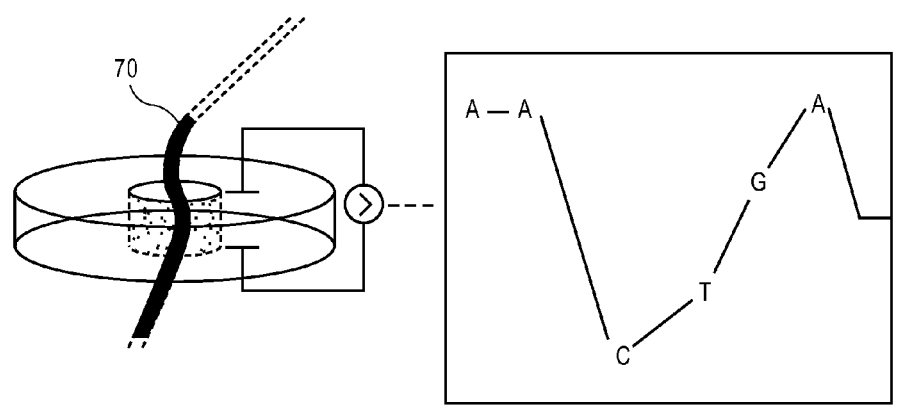
FIG. 4 is a schematic illustration of how the sensor of FIG. 1 could be use to sequence a nucleotide strand.

FIG. 4 is a schematic illustration of a sensor of the present disclosure sequencing a DNA sample. As shown, a single-stranded DNA is threaded through the pore of the sensor. As each nucleotide in the sequence approaches the semi-conductor material, the semi-conductor material undergoes a change in conductivity which is detected by the conductivity monitor. In this example, the conductivity monitor is in communication with a signal generator which records or displays changes in conductivity over time. For example, conductivity may be the signal generator may present time-sequenced numbers presented on a graph for visual review by a user, where various peaks and valleys on the graph correlate to various target elements within the electrolyte solution as they pass through the semiconductor pore. According to some embodiments, the sensor may be able to detect and sequence double stranded DNA if it is designed to effectively detect and identify a characteristic signature from each of the paired bases.

In general, the charged body to be detected can be prepared simply by suspending it in the electrolyte solution without the need for amplification.

Of course it will be understood that while the construction of the detector is relatively simple, the data generated by the sensor identifying the changes in conductivity of the semiconductor material is not helpful without establishing what those signal changes correlate to. For example, in order to properly sequence a DNA strand, one would need to know what signal corresponds to (and thus distinguishes) each of the nucleotides adenine, cytosine, thymine, and guanine, commonly referred to as A, C, T and G. Of course it will also be understood that the signal indicating the presence of any specific target will differ depending on a variety of factors including, but not necessarily limited to, the target itself, the size, shape, arrangement, material composition, and doping level of the semiconductor material and the type and make up of the electrolytic solution.

According to one embodiment, one could simply establish baseline signals by repeatedly exposing a specific sensor configuration to a known target and determining the expected signal.

Additional guidance with regard to the design and operation of the sensor may be obtained by reviewing Fleherty et al, "Manipulating Semiconductor Colloidal Stability Through Doping," Phys. Rev. Ltt., 113 (2014) pp. 158302 and Fleherty et al., "Charge regulation at semiconductor-electrolyte interfaces," J. Coll. Int. Sci., Vol. 449, (2015) pp 409-415, both of which are hereby incorporated by reference and which discuss the basic principal behind the presently described sensor. Those of skill in the art will understand that this information could be used to optimize a system for detection of a particular target, for example, by enabling the design of a system that will produce the greatest signal differences between detectable species (for example, in a sequencing application, the sensor could be optimized to produce the greatest signal differences between the different nucleotides) so as to create higher confidence in the results.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for detecting an unlabeled target in an electrolyte solution comprising:
   providing at least one detecting unit comprising a doped semiconductor material having a pore and a detector configured to measure the conductivity of the doped semiconductor material surrounding the pore; and
   flowing the electrolyte solution comprising the unlabeled target through the pore;
   wherein a change in the local conductivity of the doped semiconductor material surrounding the pore as the unlabeled target passes through the pore indicates the presence of the unlabeled target in the electrolyte solution.

2. The method of claim 1 wherein the target is a polymer and changes in local conductivity of the doped semiconductor material surrounding the pore enables the identification of one or more monomer within the polymer.

3. The method of claim 2 wherein the polymer is a nucleic acid sequence and changes in local conductivity of the doped semiconductor material surrounding the pore enables the identification of each nucleotide in the nucleic acid sequence in order.

4. The method of claim 3 wherein the nucleic acid sequence is single-stranded.

5. The method of claim 3 wherein the nucleic acid sequence is double-stranded.

6. The method of claim 2 wherein the polymer is an amino acid sequence and the changes in local conductivity of the doped semiconductor material surrounding the pore enables the identification of each amino acid in the amino acid sequence in order.

7. The method of claim 1 wherein the detecting unit is part of a plurality of detecting units, wherein each detecting unit within the plurality comprises a doped semiconductor material having a pore and wherein all of the pores are in fluid communication with each other.

8. The method of claim 7 wherein at least two of the detecting units are identical in shape and composition.

9. The method of claim 7 wherein at least two of the detecting units differ in either shape, composition, or both.

10. The method of claim 9 wherein at least one of the detecting units comprises a first pore formed within an n-doped semiconductor material and at least one of the other detecting units comprises a second pore formed within an p-doped semiconductor material.

11. A method for detecting a target in an electrolyte solution comprising:
    providing at least one detecting unit comprising a doped semiconductor material having a pore and a detector configured to measure the conductivity of the doped semiconductor material surrounding the pore; and
    flowing the electrolyte solution and target through the pore;
    wherein the passage of the target through the pore changes the local conductivity of the doped semiconductor material surrounding the pore; and
    detecting the change in the local conductivity of the doped semiconductor material.

12. The method of claim 11 further comprising obtaining the target and suspending it in electrolyte solution without modifying the target by adding a label.

13. The method of claim 11 further comprising suspending the target in electrolyte solution without amplifying the target.

* * * * *